(12) United States Patent
Molebny

(10) Patent No.: US 6,715,877 B2
(45) Date of Patent: Apr. 6, 2004

(54) METHOD OF MEASUREMENT OF WAVE ABERRATIONS OF AN EYE AND DEVICE FOR PERFORMING THE SAME

(76) Inventor: Vasyl Molebny, 6 Velyka Kytaivska St., apt. 9, 03028 Kiev (UA)

( * ) Notice: Subject to any disclaimer, the term of this patent is extended or adjusted under 35 U.S.C. 154(b) by 0 days.

(21) Appl. No.: 10/259,673

(22) Filed: Sep. 30, 2002

(65) Prior Publication Data

US 2003/0063257 A1 Apr. 3, 2003

(30) Foreign Application Priority Data

Mar. 10, 2001 (UA) ........................................ 2001106765

(51) Int. Cl.[7] .............................................. A61B 3/10
(52) U.S. Cl. ..................................................... 351/211
(58) Field of Search ................................ 351/205, 206, 351/211, 212, 216, 221, 246; 356/511, 512, 515

(56) References Cited

U.S. PATENT DOCUMENTS 6,572,230 B2 * 6/2003 Levine ...................... 351/221
6,595,642 B2 * 7/2003 Wirth ......................... 351/211
6,631,991 B2 * 10/2003 Wirth ......................... 351/211

\* cited by examiner

Primary Examiner—George Manuel
(74) Attorney, Agent, or Firm—I. Zborovsky

(57) ABSTRACT

Measurement of wave abberations of eye is performed by probing the eye with a narrow beam of laser radiation and measuring the wave front tilts in subapertures of radiation, exiting back from the eye, by of a Hartman-Shack sensor. In the process of measurements, dosed tilts are introduced into the wave, repeated several times with varied tilts of the beam as a whole during each subsequent measurement, and the reconstruction of the wave front is performed in accordance with the data obtained in all angular positions of the beam. The device for measurement includes a probing channel, a measuring channel and a channel of positioning. For controlling the wave front, a unit of dosed tilting of the wave front is introduced, based on the acousto-optic deflector, in the first embodiment—in the measuring channel, and in the second embodiment—in the probing channel. A wider dynamic range of measured wave aberrations of the human eye is achieved.

19 Claims, 17 Drawing Sheets

METHOD OF MEASUREMENT OF WAVE ABERRATIONS OF AN EYE AND DEVICE FOR PERFORMING THE SAME

BACKGROUND OF THE INVENTION

The invention relates to medical instrumentation, in particular to diagnostic measuring instrumentation for refractive surgery, and can be used for optometric investigations of vision and high quality laser-based operations of vision correction.

Methods and devices for investigation of aberrations of the optical system of an eye as a function of spatial pupil coordinates are known. Publication of R. H. Webb, et al. Measurement of ocular local wave front distortion with a spatially resolved refractometer. *Applied Optics*, 1992, Vol. 31, pp. 3678–3686 describes measurement of the optical power of an eye in different points of entrance pupil. The disadvantage of this implementation of Scheiner principle follows from the direct participation of the patient in the procedures of aberration measurements, it means, the measurements are subjective. They require considerable time, tiring the patient, and leading to low accuracy because of unstable accommodation state of the eye, eye movements in the process of measurements, etc.

Methods and devices for objective measurement are known as well. In one of them, described, e.g., in the publication of M. Mrochen, et al. Principles of Tscherning aberrometry. *Journal of Refractive Surgery*, 2000, Vol. 16, pp. 570–571, a regular light pattern is projected on the retina, its distortions being correlated with aberration parameters of the optical system of the eye. In addition to the disadvantages of technical nature (difficulties with identification of some details of the distorted regular light pattern), the method has a fundamental disadvantage: measured distribution of aberrations is inadequate to the distribution formed by a beam of rays coming from infinity and focused on the retina.

The skiascopic principle is known of projecting moving strips of light on retina. Light backscattered from retina is detected by a set of photodetectors, characteristics of refraction are determined from temporal dependencies in the detected pulse signals for different orientations of the projected light pattern (see for example S. MacRae, et al. Slit skiascopic-guided ablation using the Nidek laser. *Journal of Refractive Surgery.* 2000, Vol. 16, pp. 576–580). The drawback of this technique is in the difficulty of its realization requiring a large number of movable mechanical parts and still having low resolution of measurements.

According to the ray tracing technique for measurement of refraction aberrations, known from the patent application of Ukraine (V. V. Molebny, et al. Device for measuring aberration refraction of the eye. Patent Application of Ukraine No. 98105286, Int. Cl. A61B 3/00, A61B 3/10, A61B 3/14, filed Oct. 7, 1998, which is now the Ukranian Patent 46,833 published Jun. 17, 2002. See also; U.S. International Patent Application PCT/US99/23327, Int. Cl. A61:3 3/00, filed Oct. 7, 1999, International Publication Number WO 00/19885, Apr. 13, 2002. Ray tracing technique is also a part of the U.S. Pat. No. 6,409,345 to V. Molebny, et al. Issued Jun. 25, 2002.), entrance aperture of the eye is scanned by a narrow laser beam in parallel to the line of patient's sight, and coordinates of its projection on retina are measured sucessively in time. Map of refraction errors is reconstructed from these data.

For parallel (in time) measurement of wave aberrations, measurement of wave front structure is used at the exit of the eye by means of partitioning this structure into subapertures. This method, described in the patent issued to D. R. Williams, et al. (Rapid, automatic measurement of the eye's wave aberration. U.S. Pat. No. 6,199,986. Int. Cl. A61B 3/10, Mar. 13, 2001), is chosen for a prototype. In accordance With said method, a narrow beam of laser radiation is directed into the eye, the component backscattered by the retina is selected from the radiation returning from the eye, this selected radiation is divided into subapertures by means of a lenslet array, the wave front tilt in each subaperture is determined by measuring the shift of the focal spot position in regards to the optical axis of the corresponding lens of said lenslet array. The wave front is reconstructed from its tilts in separate subapertures and the wave front aberrations are calculated as coefficients at Zernike polynomials, defining the wave front surface.

Difficulties in identification of focal images formed simultaneously in all subapertures are distinctive for this method. They result in narrower dynamic range of the measured aberrations down to ±3 diopters, that is insufficient for practical use. The range could be made wider at the expense of wider subapertures, but it would result in lower spatial resolution of measurements. In the same manner, making higher the spatial resolution at the expense of larger number of analyzing subapertures would result in narrower dynamic range of aberrations to be measured. To speak shorter, we shall define both these mutually dependent phenomena as the same drawback—narrow dynamic range

SUMMARY OF THE INVENTION

Accordingly, it is an object of the present invention to provide a new method of measurement of wave aberrations of an eye and device for performing the same.

The first invention of the group has an objective of making wider dynamic range of the measured wave aberrations of a human eye, without reducing the number of analyzing subapertures. This objective is resolved by probing the eye with a narrow beam of laser radiation, selecting the component of the radiation scattered by the retina and exited back from the eye, partitioning said component into subapertures by a lenslet array, measuring the wave front tilt in each subaperture by determining the shift of the position of a focal spot in regards to the optical axis of each lens, reconstructing the wave front in accordance with measured tilts thereof in separate subapertures and calculating aberrations of the wave front as coefficients of Zernike polynomials representing its surface, wherein the wave front tilts in the subapertures are measured several times with a tilt of the beam of laser radiation varied in each subsequent measurement within the angular range between the neighboring subapertures, and the reconstruction of the wave front is performed from the data obtained at all angular positions of the beam, with consideration of the tilts of the beam varied in each measurement.

In each measurement with a varied tilt of the wave front, focal images in the subapertures are shifted, that is equivalent to another measurement with an additional lenslet array. As a result of several measurements, data are obtained which are equivalent to the data obtainable by means of a lenslet array with a larger number of subapertures. In this way, while maintaining a wide dynamic range of measured aberrations which corresponds to the selected density of subaperatures, spatial resolution is increased due to the fact that, for the sake of wave front reconstruction, the amount of data on wave front tilts is increased several times, that is equivalent to the several times larger number of subapertures.

Device, implementing the proposed method, considers also the modality of its positioning and orienting as well as controlling the accommodation state of the eye, these procedures are not important from the point of view of the sequence of operations, but are needed for obtaining correct results by means of the device. These components are present also in the prototype (See the above mentioned U.S. Pat. No. 6,199,986, and also in the publication of R. Applegate, et al. Optics of aberroscopy and super vision. *Journal of Cataract and Refractive Surgery.* 2001, Vol. 27, pp. 1093–1107), containing probing and measuring channels, which are separated by a polarization beam splitter, and a channel of positioning, orientation and providing an accommodation state of the eye. The probing channel is composed of a laser and a telescope functioning as a beam former, while the measuring channel is composed of a relay lens, a lenslet array and a matrix of position-sensing photodetectors installed in their foci, and connected to a signal former, which is linked to a computer performing the functions of the device control, of reconstruction of the wave front and of calculation of wave aberrations.

The disadvantage of the prototype is in its incapability to widen the dynamic range of measured aberrations, for example, at the expense of increase in sizes of analyzing aperatures without reduction of spatial resolution.

To implement the proposed method into a device, an objective is set for said device to increase the dynamic range of measured wave aberrations due to introduction of additional components and links, this objective is to be achieved in two versions of the device.

In the first version of the embodiment, the device for measurement of wave aberrations of an eye, containing a probing channel and a measuring channel, separated from each other by a polarization beam splitter, and a channel of positioning, orientation and providing an accommodation state of the eye, the probing channel being composed of a laser and a telescopic beam former of radiation, the measuring channel being composed of a relay lens, a lenslet array, and a matrix of position-sensing photodetectors installed in their foci and connected to a signal former, which is linked to a computer performing the functions of the device control, of reconstruction of the wave front and of calculation of wave aberrations, wherein the measuring channel, along the path of radiation exiting from the eye, is provided with a unit of dosed tilting of the wave front, said unit of dosed tilting of the wave front being located between the relay lens and the lenslet array, wherein said unit of dosed tilting of the wave front includes a two-coordinate acousto-optic deflector, a telescope-selector, a driver of the acousto-optic deflector and a frequency synthesizer so that the two-coordinate acousto-optic deflector and the telescope-selector are arranged in series, outputs of the driver are connected to the acousto-optic deflector and the output of the frequency synthesizer is connected to the input of the driver, and its controlled input is linked to the computer.

Such a construction of the device, using the unit of dosed tilting of the wave front, which is introduced directly into the measuring channel, allows to vary the tilts in all subaperatures simultaneously and to thus shifting the focal images in each subaperature by the same value that, as a result, is equivalent to the action of several lenslet arrays or, in other words, is equivalent to obtaining data with a lenslet array having a larger number of subapertures.

In the second version of the instrumental embodiment of the proposed method, the control of the wave front tilt of the radiation, exiting from the eye, is performed indirectly due to shifting the laser beam projection on the retina which is a secondary source of radiation. For this purpose, into the device for measurement of wave aberrations of an eye, containing probing and measuring channels, separated from each other by a polarization beam splitter, and a channel of positioning, orientation and providing an accommodation state of the eye, the probing channel being composed of a laser and a telescopic beam former of radiation, the measuring channel being composed of a relay lens, a lenslet array, and a matrix of position-sensing photodetectors installed in their foci and connected to a signal former, which is linked to a computer performing the functions of the device control, of reconstruction of the wave front and of calculation of wave aberrations, namely, into the probing channel, after the telescopic beam former, a unit of dosed tilting of the wave front is introduced, wherein said unit of dosed tilting of the wave front includes a two-coordinate acousto-optic deflector, a telescope-selector, a scan converter, a driver of the acousto-optic deflector and a frequency synthesizer, so that the two-coordinate acousto-optic deflector, the telescope-selector and the scan converter are arranged in series, outputs of the driver are connected to the acousto-optic deflector, the output of the frequency synthesizer is connected to the input of the driver, and its controlled input is linked to the computer.

The device according to the second embodiment is designed in such a way that the probing ray enters the eye always through the same point of the cornea, regardless of the tilt of the ray. The tilted probing ray is projected on the retina with a shift, resulting in the tilt of the exiting radiation. In its other attributes, the second embodiment is the same as the first one, meaning that the tilts of the exiting wave front are performed simultaneously in all subaperatures, due to the unit of dosed tilting of the wave front introduced in the probing channel, so as to provide shifts of the focal images in each subaperature by the same value, which, as a result, is equivalent to the superposition of action of several lenslet arrays, or, in other words, equivalent to obtaining data corresponding to a lenslet array with a larger number of subaperatures.

Due to the proposed construction of the devices for measurement of wave aberrations of the human eye and introduction of the described interactions, the possibility of unambiguous identification is achieved of light spots in the plane of the matrix of position-sensing photodetetors, enabling to avoid essential disadvantage, namely a narrow dynamic range of the measured deviations of the wave front, and to make wider the dynamic range of the measured wave aberrations of the human eye with a given spatial resolution or to increase spatial resolution at a given dynamic range of measured wave aberrations.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
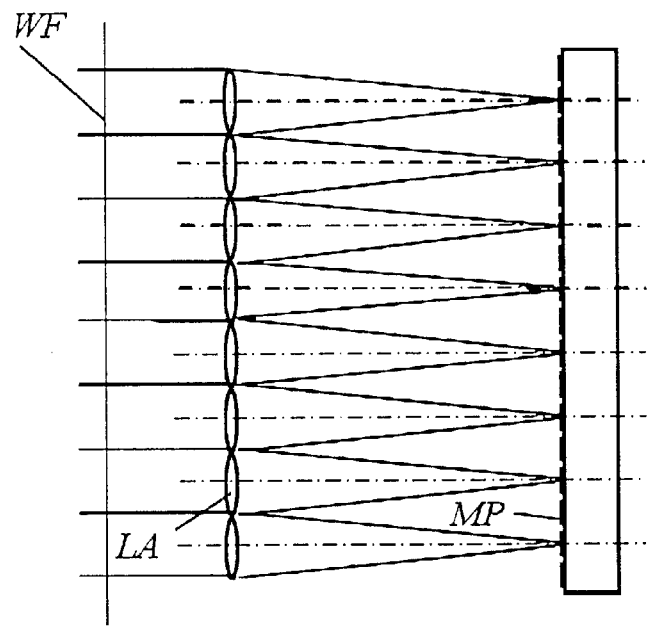
FIG. 1. Partitioning of the wave front into subaperatures: WF—wave front; LA—lenslet array, MP—matrix of position-sensing photodetectors.
Figure 2:
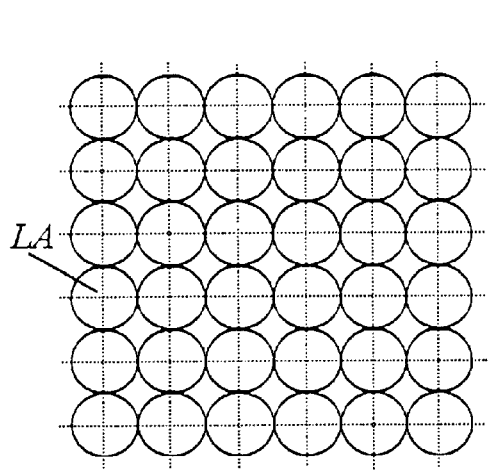
FIG. 2. Front view of the lenslet array LA.
Figure 3:
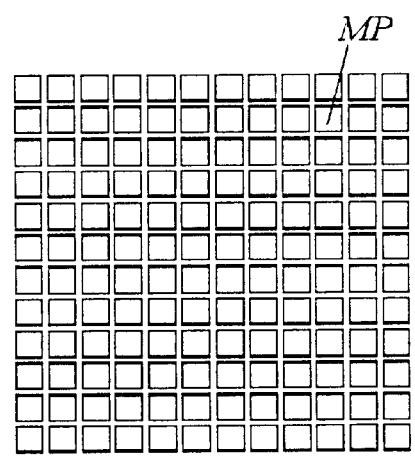
FIG. 3. Front view of the matrix of photodetectors MP.
Figure 4:
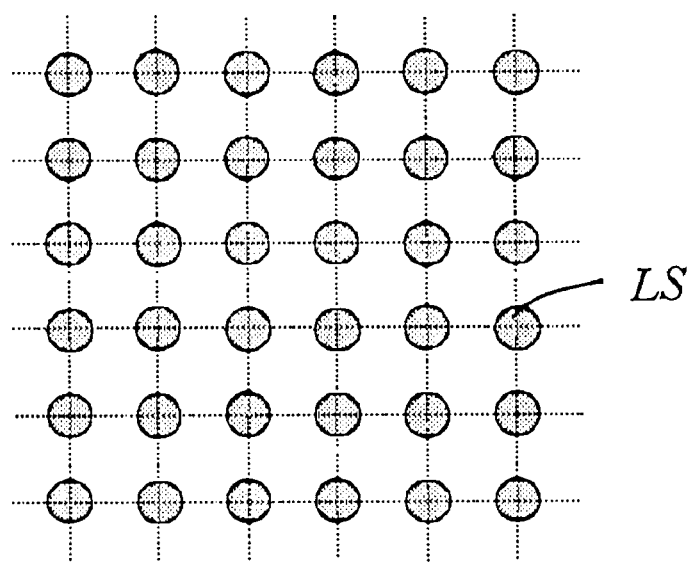
FIG. 4. Light spots LS in the focal plane with a plane wave front.

Confirmation of the possibility of implementation of the first out of the group of inventions, namely, of the method of measurement of wave aberrations of the eye, is illustrated in FIGS. 1 through 15. Let us analyze them in detail. As indicated, a parallel beam of light is directed into the patient's eye. It can be wide so as to occupy the whole entrance aperture of the eye, or (better) narrow, with a diameter of less than 1 mm, and is introduced into the eye as a rule in its axial zone. This beam of light is focused on the retina which scatters the light with an indicatrix having also a mirror component. Light exiting from the eye with the wave front WF is divided into subapertures by means of a lenslet array LA (FIG. 1), and projected onto a matrix of position-sensing photodetectors MP. Cross-section (front view) of the lenslet array is shown in FIG. 2. For complete coverage of the cross-section of the beam, subapertures can have hexagonal shape. Incomplete coverage allows lens diameters to be smaller than distance between them. The matrix of position-sensing photodetectors (FIG. 3) can be, for example, a matrix of charge-coupled devices CCD, very popular for use in TV cameras. A combination of lenslet array with matrix of position-sensing photodetectors is called Hartmann-Shack sensor.

Figure 5:
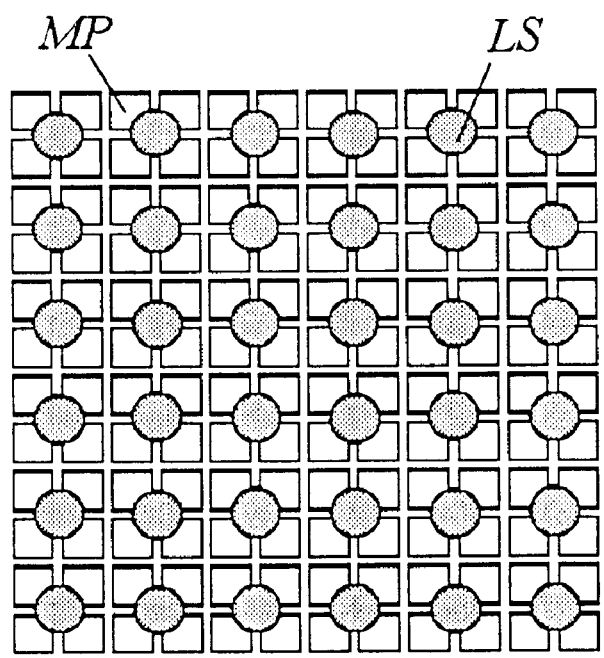
FIG. 5. Light spots LS formed by a plane wave front on the matrix of position-sensing photodetectors MP.

In the case of emmetropic eye, i.e., of an eye whose optical system has no aberrations, wave front exiting from the eye will be plane, and all elementary beams passing through the lenslet array will be focused on the optical axes of the lenses of this array as light spots LS (FIG. 4), and said pattern of light spots LS appears on the matrix of the position-sensing photodetectors MP which corresponds to untilted wave front in each point of the exit aperture of the eye (FIG. 5).

Figure 6:
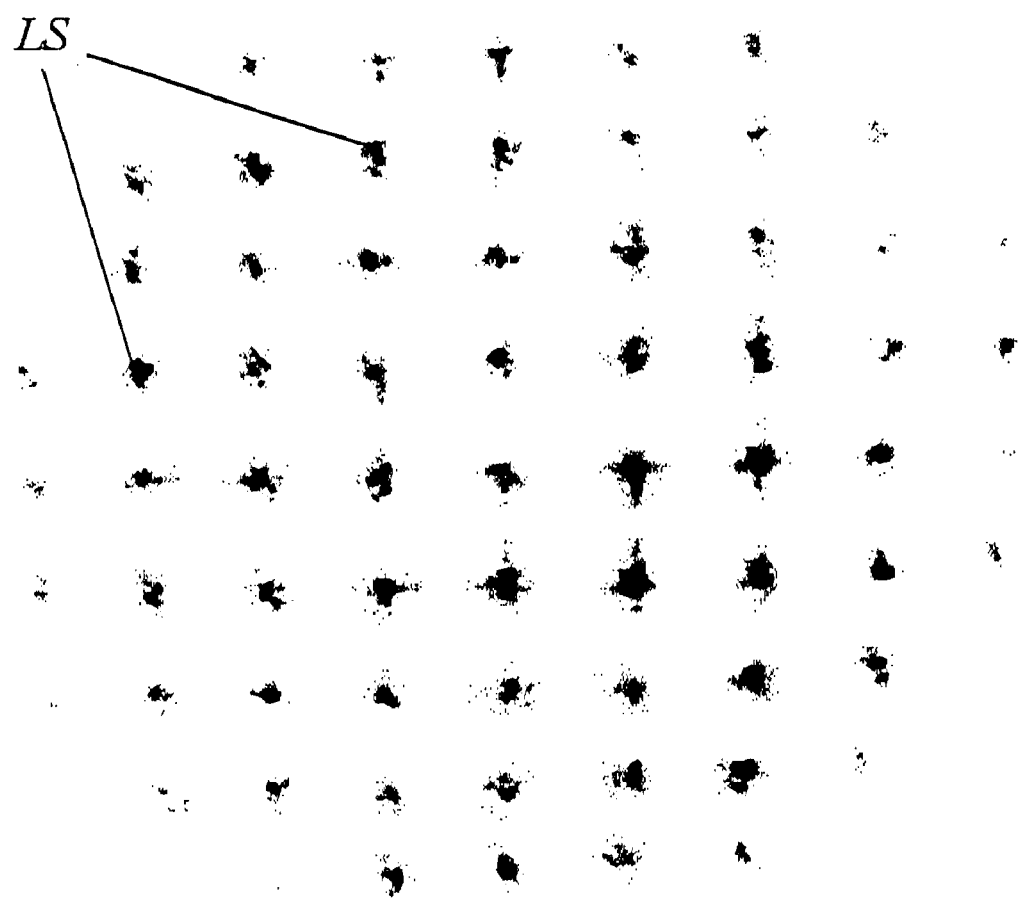
FIG. 6. Structure of light spots LS in the focal plane of the lenslet array formed by a beam of laser radiation, exiting from the eye with insignificant distortions of the wave front by eye structures.
Figure 7:
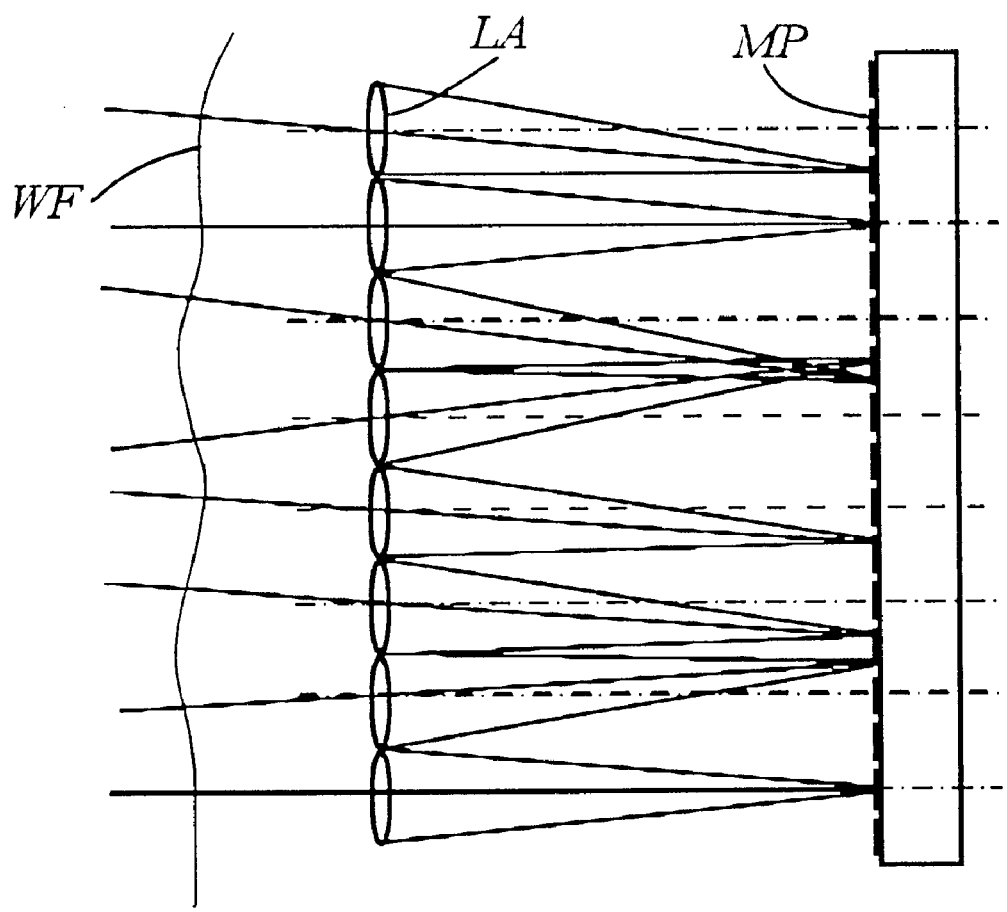
FIG. 7. Projection of significantly distorted wave front WF on the plane of the matrix of position-sensing photodetectors MP made by means of the lenslet array LA.
Figure 8:
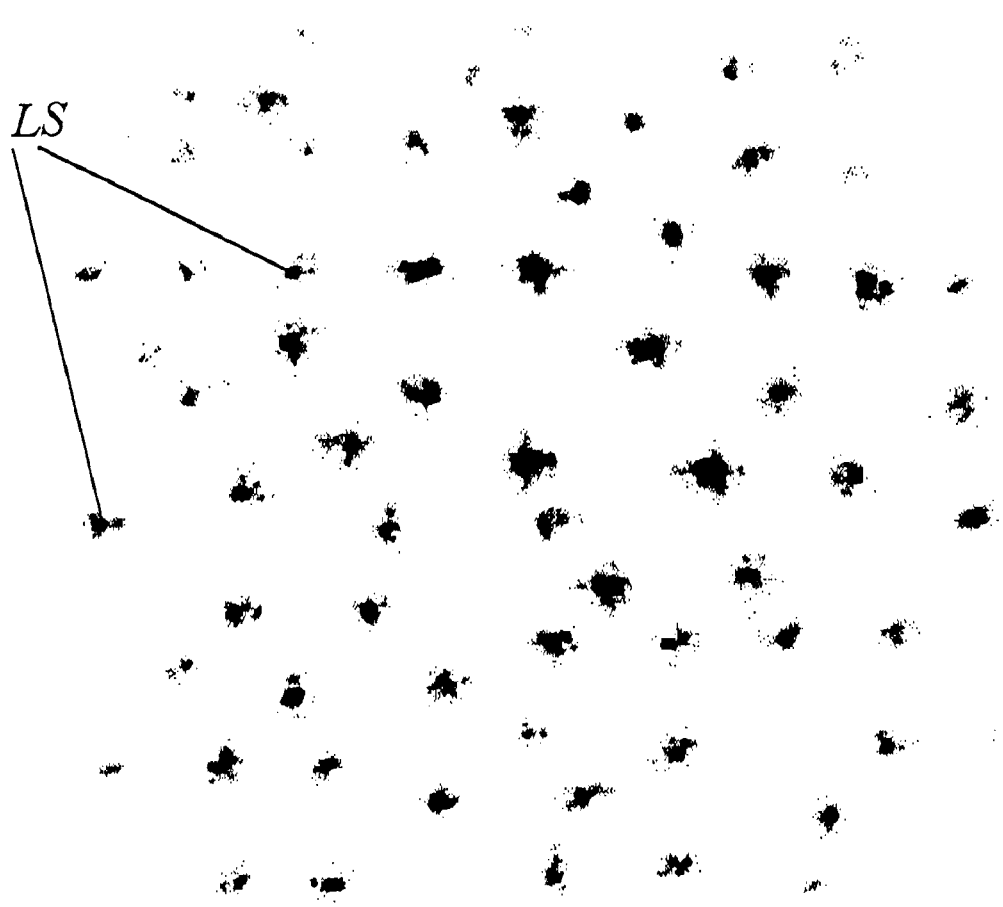
FIG. 8. Structure of light spots LS in the focal plane of the lenslet array formed by a beam of laser radiation, exiting from the eye with significant distortions of the wave front by eye structures.

When implementing this method with coherent light, the spots will have non-uniform shape in the foci of lenslet array, distorted by the speckle structure (FIG. 6). In the case of insignificant aberrations, each element of the spot pattern can be unambiguously identified.

More complicated situation occurs in the process of investigation of an ametropic eye with high level of aberrations. In this case, focal spots can approach each other significantly, or even overlap, or pass one behind the other (FIG. 7), so that their unambiguous identification, as can be seen from FIG. 8, becomes impossible. One can reduce the number of elements of the lenslet array so as to provide the identification of the focal spots, however this will lead to a loss of spatial resolution of measurements.

It is proposed to resolve in time the measurements in neighboring points, i.e., to create several "rarefied" structures, by means of which, measurements are performed not simultaneously, but in successive moments of time, and the locations of these "rarefied" structures are such that with their superposition over one another, a sum structure will be formed with high spatial resolution.

Figure 9:
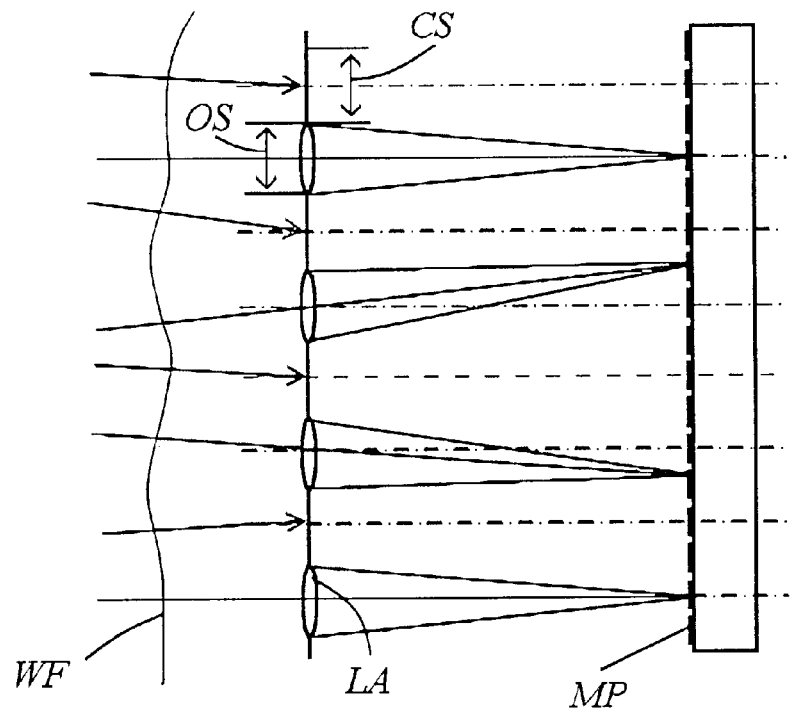
FIG. 9. Projection of significantly distorted wave front WF on the plane of a matrix of position-sensing photodetectors MP made by means of a rarefied lenslet array LA; rarefied structure starting with closed sections CS.
Figure 10:
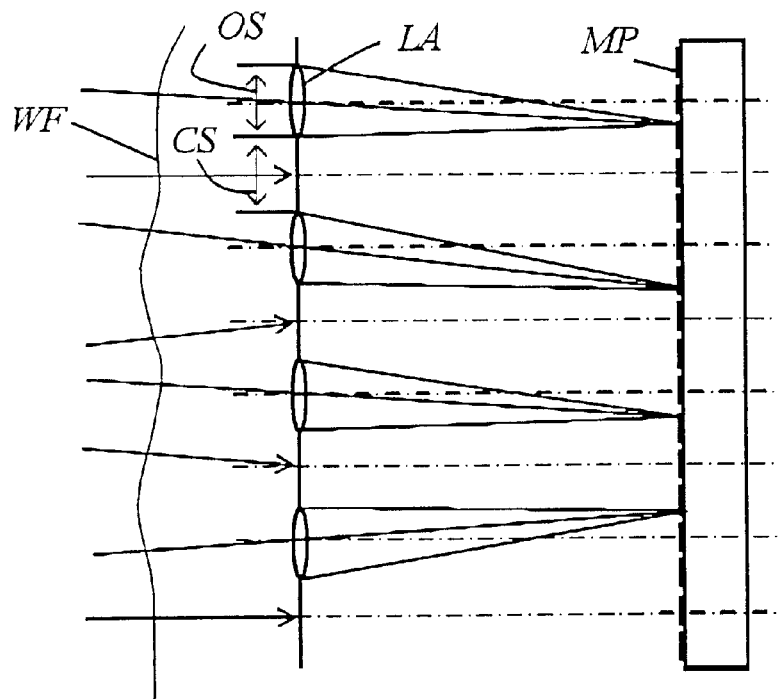
FIG. 10. Projection of significantly distorted wave front WF on the plane of a matrix of position-sensing photodetectors MP made by means of a rarefied lenslet array LA; rarefied structure starting with open sections OS.
Figure 11:
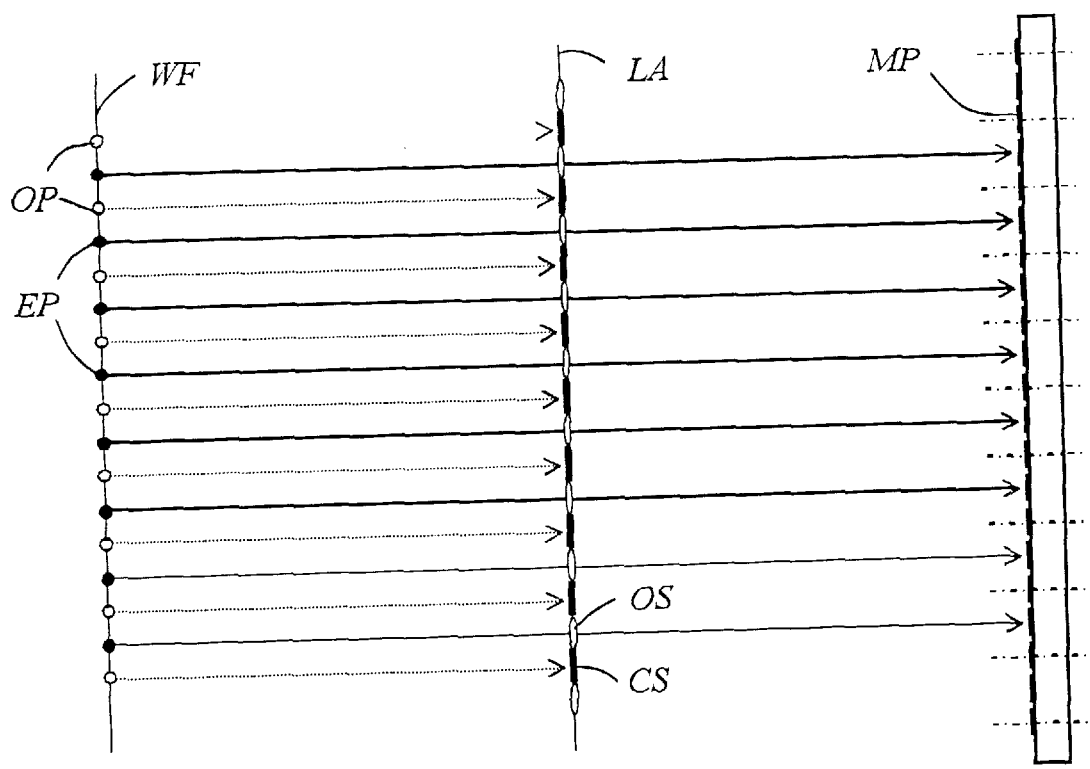
FIG. 11. Projection of a plane wave front WF made by means of the rarefied lenslet array LA (normal impingement), odd beams falling on closed sections CS of the lenslet array; OP—odd points of the wave front, through which odd beams pass, EP—even points of the wave front through which even beams pass.
Figure 12:
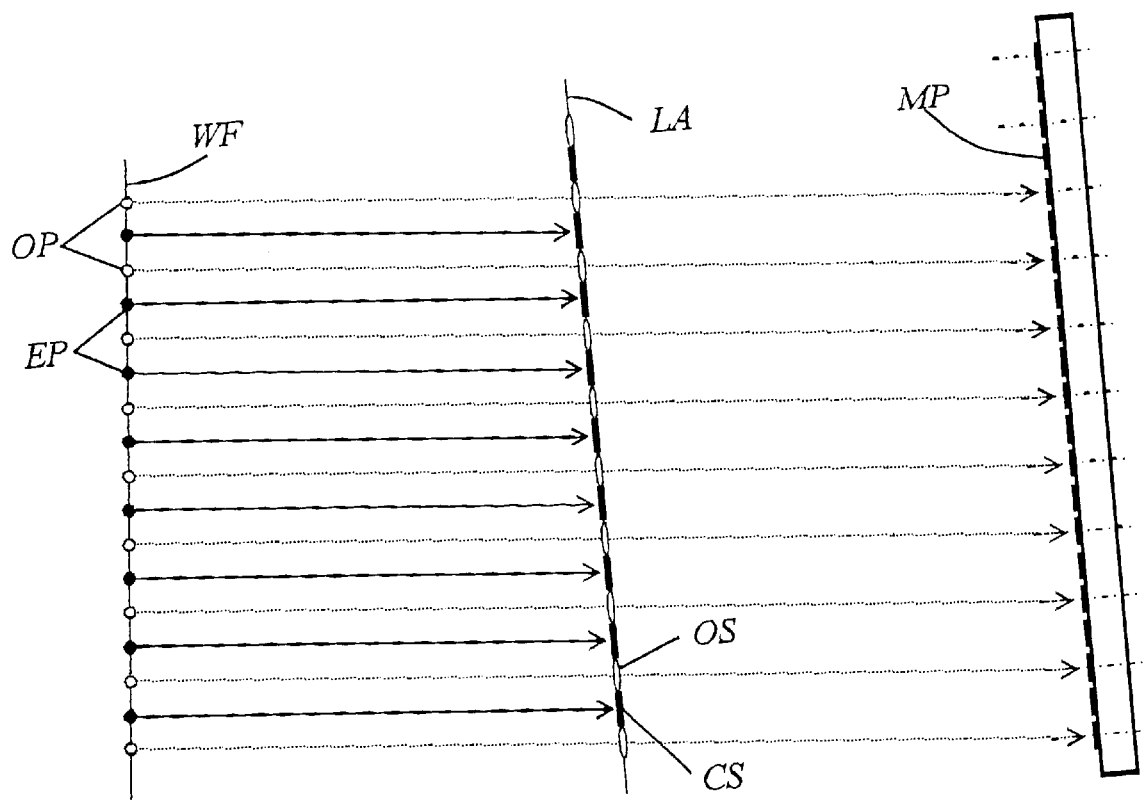
FIG. 12. Projection of a plane wave front WF by means of the lenslet array LA (inclined impingement); odd beams falling on the open sections OS of the lenslet array.

This principle is illustrated in FIG. 9 and FIG. 10 where the wave front WF is projected on the matrix of position-sensing photodetectors MP by means of the lenslet array LA with a "rarefied" structure, which has closed CS and open OS sections.

In the first step, the wave front is projected through the lenslet array with an "even" location of the open OS and closed CS sections (FIG. 9). In a next step (in a subsequent moment of time), the wave front passes through the lenslet array with "odd" location of the open and closed sections (FIG. 10).

Obviously, in the first and second steps, these structures operate as "rarefied", in which all focal spots are identified. A sum of obtained results will correspond to the structure with a double density of the lenslet array. As will be shown farther, in a two-dimensional case, this will be equivalent to a four times increase in the density of the lenslet array.

A simplest technical solution, that could resolve said measurements in time by means of rarefied structures, could be performed by means of a spatial modulator opening and closing separate sections of the lenslet array to form corresponding rarefied structures. This approach would be complicated and expensive, since it would require creation of structures of spatial modulators and lenslet arrays corresponding to one another with high precision.

We propose to move "rarefied" structure stepwise along the wave front in the process of measurements by means of wave front tilting. This principle is explained in FIG. 11 and FIG. 12.

In the structure of adjacent points in the to-be-analyzed wave front cross-section WF, we shall indicate "odd" (non-hatched) and "even" (hatched) points, through which correspondingly odd and even rays (beams) pass. Let us assume that we have such a structure of the lenslet array LA which, in the case of normal orientation of the wave, allows the passage of the even beams and does not allow passage of the odd beams. On the matrix of photodetectors, a rarefied focal-plane image is obtained. Now let us incline the wave front so that (FIG. 12) the odd beams pass through the structure of the lenslet array and the even beams do not pass. A rarefied focal-plane image is obtained on the matrix of the photodetectors corresponding to the shift of subapertures of the wave front by a distance between the even and odd points. Information about aberrations of the wave front in all subapertures can be summed in accordance with the data obtained in each step of the measurements.

Figure 13:
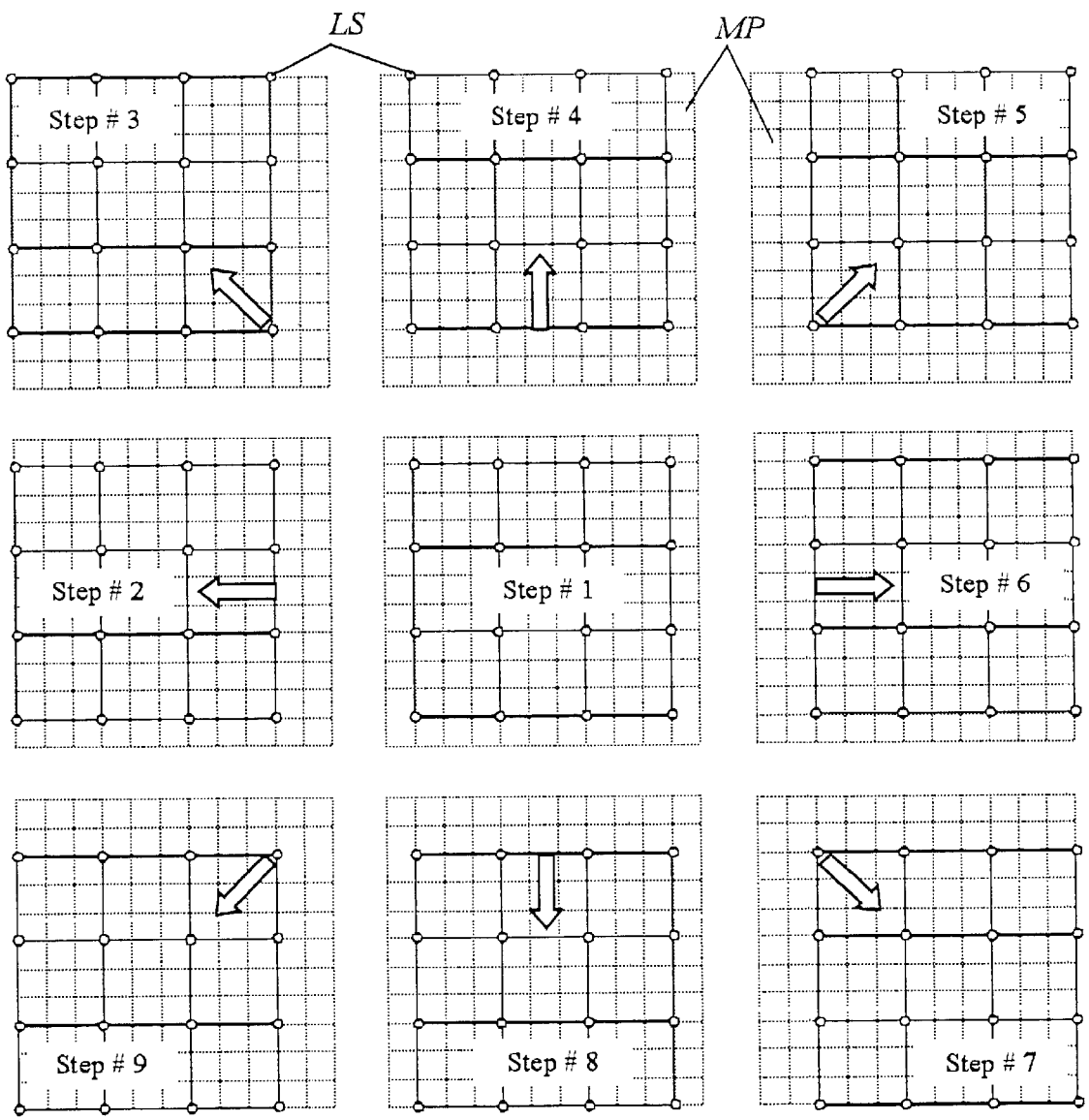
FIG. 13. Structure of light spots LS in the plane of the matrix of position-sensing photodetectors MP in the process of its formation by means of rarefied lenslet array (triple linear rarefication) in successive time moments: step #1—without additional tilt of the wave front, steps #2–9—with additional tilt of the wave front in the directions shown by arrows.

Let us examine the disposition of the focal spots in the plane of position-sensing photodetectors (FIG. 13). The structure of these photodetectors is conditionally shown in the form of a dotted grid MP, and the system of focal images (light spots) LS, projected into the plane of photodetectors, is shown in the intersections of the grid of solid lines. In the example of FIG. 13, the linear rarefication of the lenslet array is equal to three.

Measurements can be performed in the following sequence. In the first measurement (step #1), wave front of radiation exiting from the eye is projected without any tilt onto the matrix of photodetectors. Position of all focal projections is measured. In the next moment of time, a second measurement is performed with the wave front inclined so that the matrix of focal projections is displaced by one cell (in FIG. 13 to the left—step #2). Measurements with tilted wave front are repeated successively so as to cover all possible shifts (in the case shown in FIG. 13, it is one measurement without wave front tilt and eight measurements with eight different wave front tilts). Thus, in nine measurements, the grid which is linearly three times denser than the grid of the lenslet array, will be completely filled.

Figure 14:
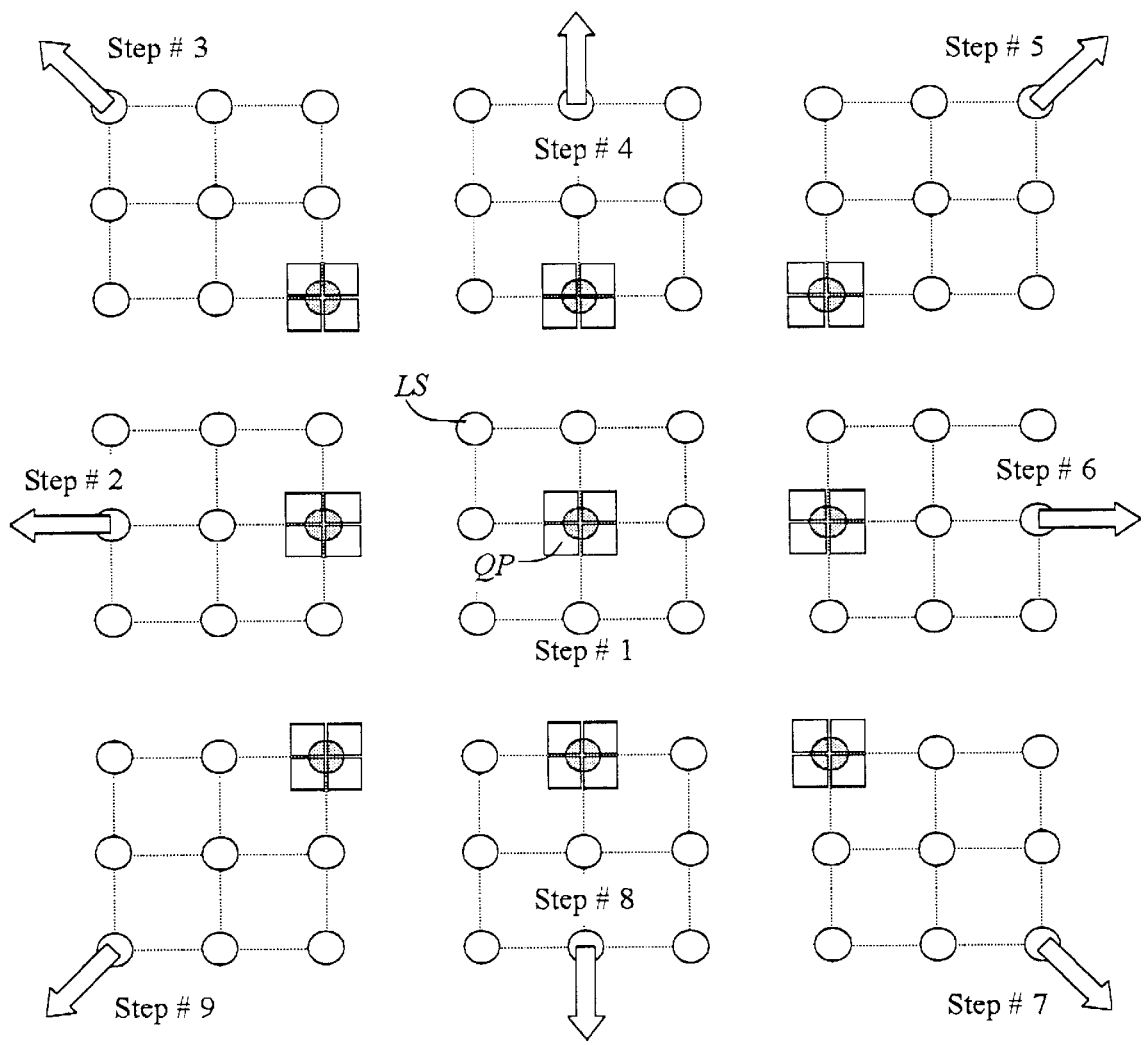
FIG. 14. Structure of light spots LS formed by means of rarefied lenslet array in successive moments of time on the same element of the matrix of position-sensing photodetectors (exemplified by a quadrant photodetector): step #1—without additional tilt of the wave front, steps #2–9—with additional tilt of the wave front in directions shown by arrows: QP—an element of a matrix of position-sensing photodetectors (quadrant photodetector).
Figure 15:
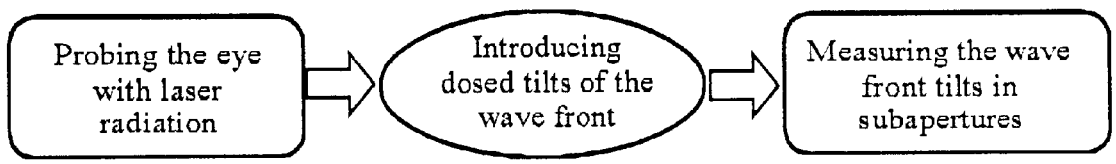
FIG. 15. Introduction of a procedure of wave front tilting into the sequence of measuring operations.

To explain this principle on the example of one element (cell) of the matrix of the position-sensing photodetectors, in FIG. 14, one element is chosen, e.g., in a form of a quadrant photodetector QP, and all mentioned steps of tilting of the wave front are shown, so that, as a result, the chosen photodetector yields, at time intervals, the information on distortions of the wave front in nine adjacent nodes of the measuring grid in which the light spots LS are projected.

Thus, in correspondence with the proposed technique, between the procedures of eye probing with laser radiation and measurement of wave front tilts in subapertures, a procedure of a stepwise dosed tilting of the wave front as a whole is introduced (FIG. 15) and repeated several times. The entire procedure of measurements of eye aberrations will have the following succession. A narrow beam of light is directed into the eye under investigation, portion of the radiation scattered by the retina is detected, and wave front tilts in subapertures are measured by means of Hartmann-Shack sensor with such a number of its subapertures which are enough for unambiguous measurements in a given dynamic range of wave front aberrations. Then, a tilt is introduced of the wave front as a whole, which is the same for the whole cross-section of the light beam exiting from the eye. The magnitude of the tilt is set within the limits of angular distance between neighboring subapertures. Measurements of wave front tilts in subapertures are performed. This operation is repeated for all possible tilts which form the measuring grid with a given density. To get the measuring grid n times larger than the linear density, $n^2$ measurements is necessary to be performed, i.e., for increasing the density of the measuring grid, for example, twice, measurements with four different wave front tilts are to be performed, etc.

Figure 16:
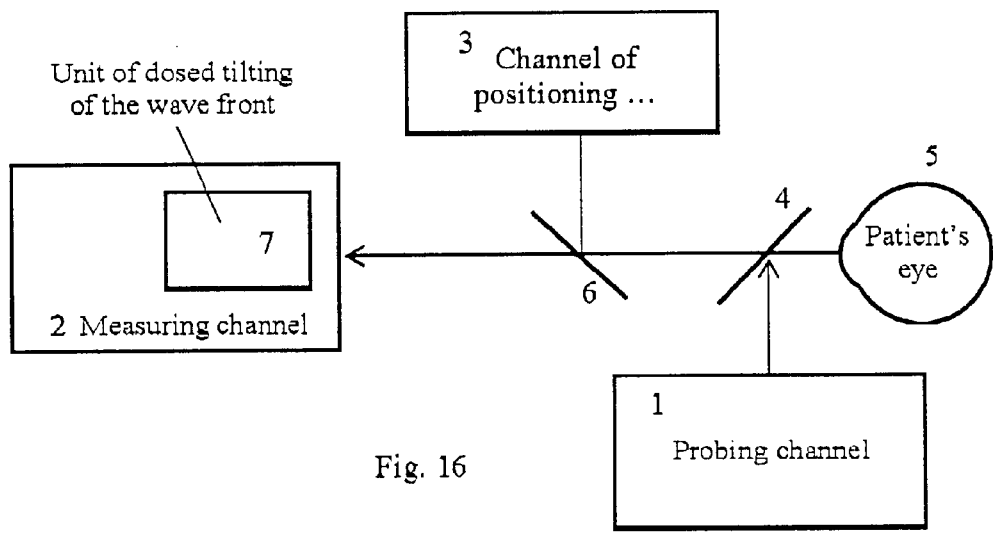
FIG. 16. Simplified structure of the device for performing the proposed method with a unit of dosed tilting of the wave front installed in the measuring channel (first version).
Figure 17:
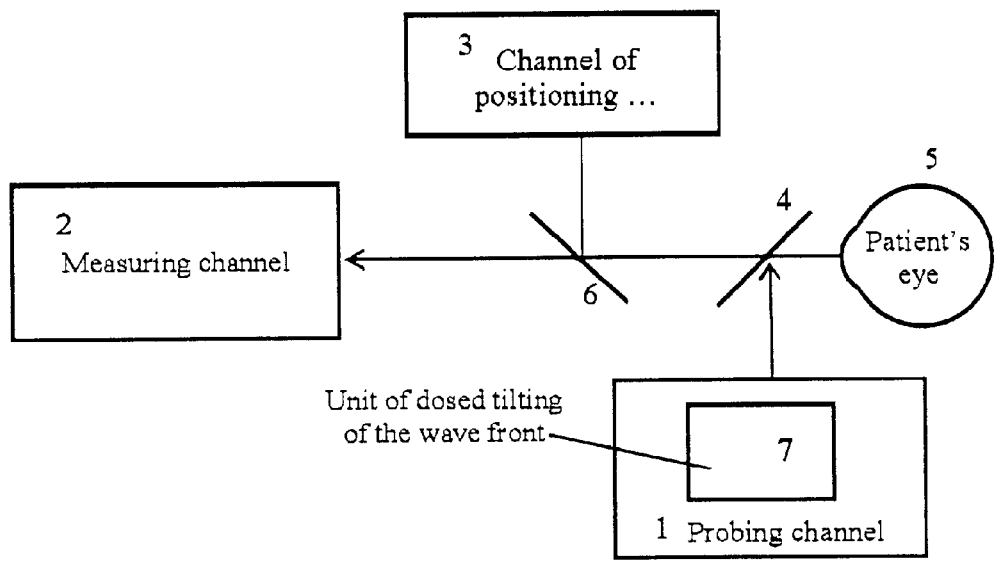
FIG. 17. Simplified structure of the device for performing the proposed method with a unit of dosed tilting of the wave front installed in the probing channel (second version).

Proposed method of measurement of the wave aberrations of an eye is performed by means of a device whose construction has two embodiments. A simplified structure of both embodiments is presented in FIG. 16 and FIG. 17. The device includes a probing channel 1, a measuring channel 2, and a channel 3 of positioning, orientation, and providing an accommodation state of the eye (abbreviated: channel of positioning). The objective of the polarization beam splitter 4 is to provide an isolation between the entrance to a patient's eye 5 from the probing channel 1 and the exit from the eye to the measuring channel 2. Similarly, a first beam splitter 6 provides joint functioning of channels 2 and 3. A unit 7 of dosed tilting of the wave front, in the first embodiment (FIG. 16), is introduced into the measuring channel 2. In the second embodiment (FIG. 17), said unit is a part of the probing channel 1.

Figure 18:
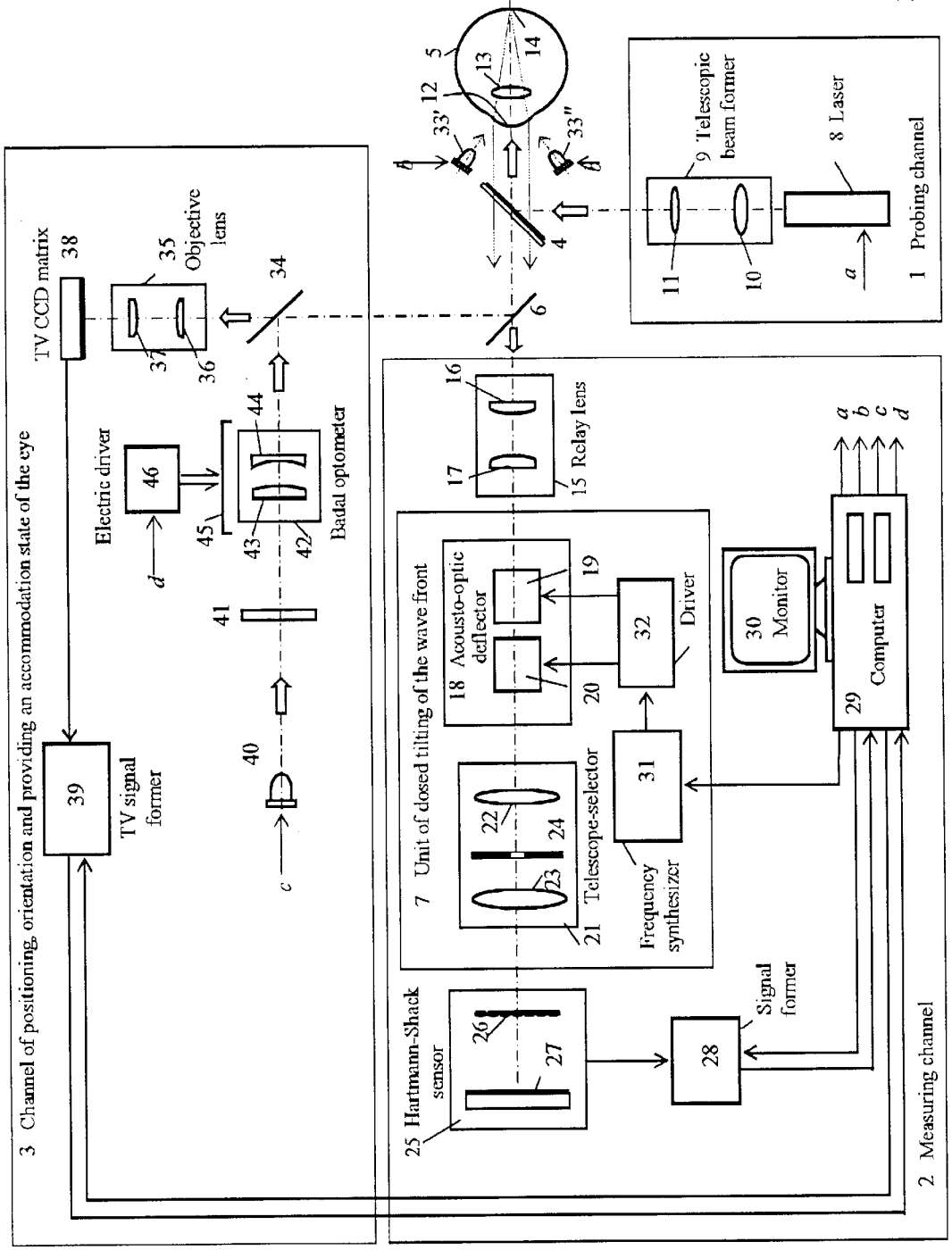
FIG. 18. Functional schematic diagram of the device for measuring wave front aberrations of an eye (first version), and a patient's eye.

Let us consider in detail the functional schematic diagram of the device for measurement of wave aberrations in accordance with the first embodiment (FIG. 18). It includes the above mentioned probing channel 1, measuring channel 2, channel of positioning 3, polarization beam splitter 4, and first beam splitter 6.

In the probing channel 1, at the exit of a light source 8, a telescopic beam former 9 is installed. Conventional laser is used as the light source, which irradiates in the near infrared part of the spectrum. It is also possible to use a laser which irradiates in the visible range. It is advisable to use a semiconductor laser, however, the type of laser is not a limitation. A cross-section of the beam of radiation of the semiconductor laser has a stretched shape, and therefore in order to provide the cross-sectional shape close to axially symmetric, the telescopic beam former 9 is composed of cylindrical lenses 10 and 11. The telescopic beam former can be designed in accordance with a Kepplerian scheme as well as in accordance with a Galilean scheme.

Polarization beam splitter 4 is set after the telescopic beam former 9. Laser radiation is directed into the patient's eye 5, whose main elements of an optical system include cornea 12, lens 13, and retina 14. Polarization beam splitter 4 reflects certain polarization (e.g., perpendicular to the plane of the drawing) in the direction of the eye, and allows the other one to pass through, this one being orthogonal, contained in the radiation exiting from the eye 5 due to depolarization of the radiation in the process of light scattering on the retina 14.

At the exit of the eye, there are successively installed a relay lens 15 composed of two lenses 16 and 17, an acousto-optic deflector 18 with units of deflection: 19—along the axis X and 20—along the axis Y, a telescope-selector 21 including two lenses 22 and 23 and a spatial filter-selector 24, a Hartmann-Shack sensor 25 composed of a lenslet array 26 and a matrix of position-sensing photo-detectors 27 (usually, it is a CCD matrix). Magnification of the telescope-selector 21 in the first embodiment of the device is usually chosen to be a unit.

A signal former 28 is connected to the output of the matrix 27, said signal former can be a standard electronic system of a television camera or a special circuit with a more oriented access to the elements of the matrix. The signal former 28 has a two-way connection with a computer 29 which contains special input/output (I/O) circuit boards for linkage with all the units exterior to the computer. The computer also includes a monitor 30. A frequency synthesizer 31 is connected with the computer, and a driver 32 is arranged at its output and has outputs connected to the acousto-optic deflector 18.

Thus, the measuring channel 2 includes the components 15–32, whereas the components 18–24 and 31, 32 form the unit 7 of dosed tilting of the wave front, said unit being introduced into the measuring channel.

Several infrared (IR) light emitting diodes (LEDs) 33 are set in front of patient's eye, two of them 33' and 33" being shown in the drawing. There can be four, six or another number of LEDs.

A first beam splitter 6 is set along the path of radiation exiting from the eye, in front of the relay lens 15. On the path of the light reflected by the beam splitter 6, another beam splitter 34 is installed. Along the way of radiation, passed through the beam splitter 34, the following components are installed: an objective lens 35 composed of lenses 36 and 37, and a television CCD matrix 38 sensitive up to infrared. A TV signal former 39 is connected to the output of the matrix 38 and linked to the computer 29.

In front of the reflecting surface of the beam splitter 34, starting from the farthest component, there are successively installed: a visible light emitting diode 40, a transparent plate 41 with deposited collimating cross-hairs, and an optical system 42 for driving patient's eye accommodation (Badal optometer), which is composed of a pancratic group of lenses 43, 44. One of the lenses is set on a movable base 45 which is mechanically connected to an electric driver 46.

Components 33–46 are parts of the channel 3 of positioning, orientation and providing an accommodation state.

Laser 8—through the link a, light emitting diodes 33—through the link b, light emitting diode 40—through the link c, and electric driver 46—through the link d are linked to the computer 29.

The above described device operates in the following manner. In correspondence with the existing practice and recommendations of the Working Group of the subcommittee of the Optical Society of America (A. Bradley, et al. Reference axis selection: A subcommittee report of the OSA working group to establish standards for the measurement and reporting of the optical aberration of the eye. In: *Vision Science and Applications*. Optical Society of America, Technical Digest, 2000, pp. 148–150), patient's eye is positioned and oriented at first in such a way, that its line of sight coincides with the optical axis of the device. For this purpose, patient has to direct his sight to the center of the collimating cross-hairs 41 which are illuminated by the light emitting diode 40. Then, the device is positioned relatively to the patient's eye so that the axis of the device passes through the center of curvature of the cornea. Correct mutual positioning and orientation of the eye and the device is indicated by a symmetrical disposition of reflexes of the light emitting diodes 33 on the screen of the monitor 30. This pattern is visualized using the television CCD matrix 38, the TV signal former 39, and an input-output interface (framegrabber) that is included in the computer 29.

When the apex of the cornea is crossed by the optical axis of the device and when the line of sight of the eye coincides with the optical axis of the device, the surface of the cornea 12, as a convex mirror, forms visible images of light emitting diodes 33 positioned symmetrically with regard to the axis of symmetry of the surface. Their secondary image in the working image plane of the objective lens 35 will be also symmetrical with regard to the optical axis of the device.

Directly before the measurements, patient has to make the eye to accommodate to a certain distance set by means of the optical system 42. The major part of the accommodation is performed by the lens 13. Most frequently, measurements are performed with the relaxed accommodation of the lens.

For this purpose, one of the lenses 43 or 44, installed on the movable base 45, is moved by means of the electric driver 46 until it reaches a position corresponding to the position of the collimating cross-hairs 41 at infinity. For better relaxation, it is even possible to "increase" this distance (by continuing to move the lens or, by means of instantaneous introduction of an additional lens), After these operations, in which a significant part is taken by an operator, the further control of the processes of measurement is performed by the computer. First, the laser 8 is turned on. Laser beam, after the telescopic beam former 9, is directed by the polarization beam splitter 4 into the patient's eye 5. This beam can be either wide or narrow. The main requirement to the beam is to form a focal spot of the smallest size on the retina 14. This can be achieved directing the beam along that path in the optical system of eye, which has the lowest aberrations. As a rule, it is the central part.

Radiation scattered by the retina and exiting from the eye, after passing through the beam splitter 6 enters the relay lens 15 whose main function is conjugation of the plane of the exit pupil of the eye, in which wave aberrations must be measured, with the plane of the lenslet array 27. From the exit of the relay lens 15, the beam of light is directed to the acousto-optic deflector 18 which includes two crystals each controlled by the driver 32. As a rule, Bragg diffraction is used, with such an orientation of the exit facet that the axis of the exiting beam, diffracted into the first order, coincided with the optical axis of the device. This condition is to be satisfied for both directions of deflection. The driver 32 is controlled from a frequency synthesizer 31, which in turn is controlled by the computer 29.

Figure 19:
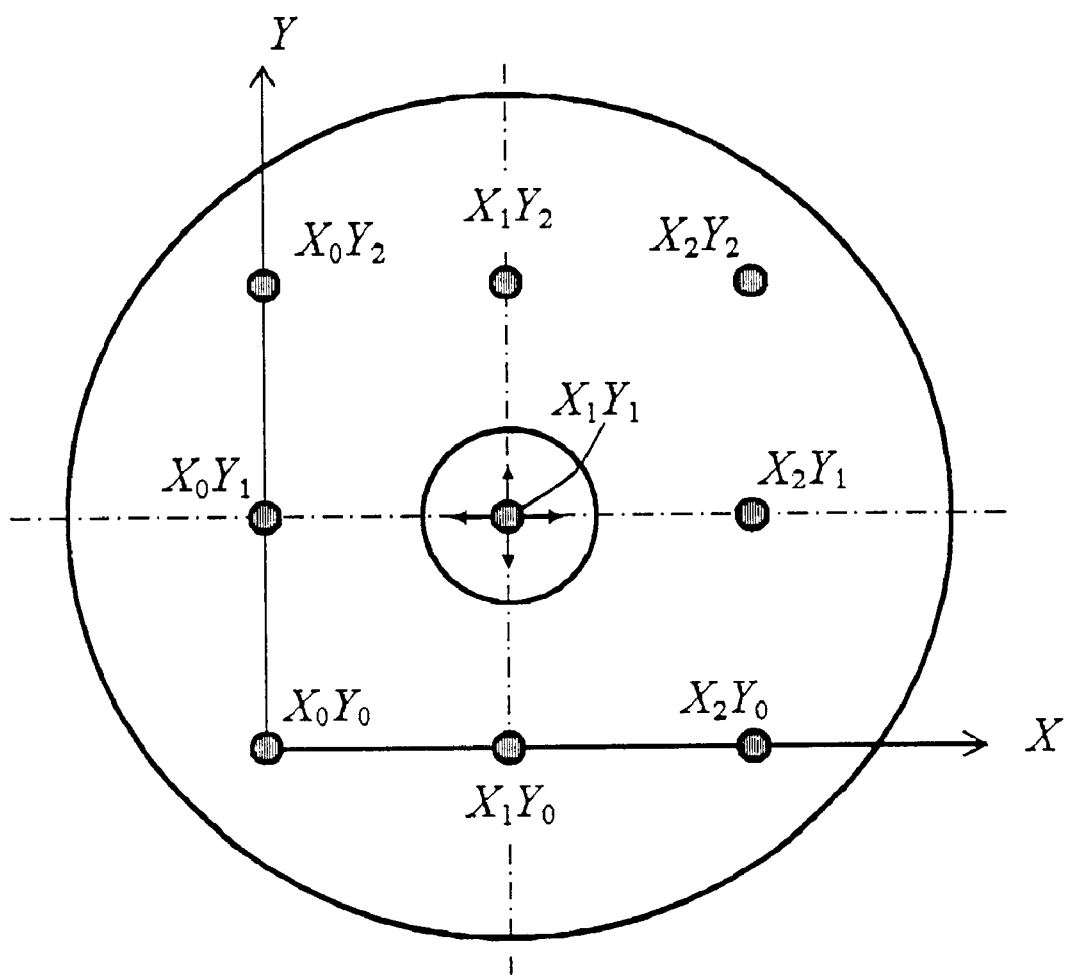
FIG. 19. Spatial filter-selector 24: X, Y—axes of coordinates of an acousto-optic deflector; $X_0$, $X_1$, $X_2$—zero, first and second orders of Bragg diffraction in the direction of the axis X at the exit from the acousto-optic deflector in the focus of the lens 22; $Y_0$, $Y_1$, $Y_2$—zero, first and second orders of Bragg diffraction in direction of the axis Y at the exit from the acousto-optic deflector in the focus of the lens 22.

From the exit of the acousto-optic deflector 18, the radiation enters the telescope-selector 21. Through the opening in the spatial filter-selector 24, only the radiation passes diffracted into the first order for both directions of the deflection (FIG. 19). In FIG. 19, directions of diffraction are identified as X and Y, and indices at X, Y represent the order of diffraction. The size of the central opening is to be no larger than enabling to pass only the radiation $X_1, Y_1$ for all possible tilts of the wave front of radiation exiting from the eye.

The wave front sensor 25 in the focal plane of the lenslet array 26 detects a plurality of focal spots created by all lenses. Position of these spots is measured by means of the matrix of photodetectors 27, and is input to computer 29 as a digital code generated by the signal former 28.

Figure 20:
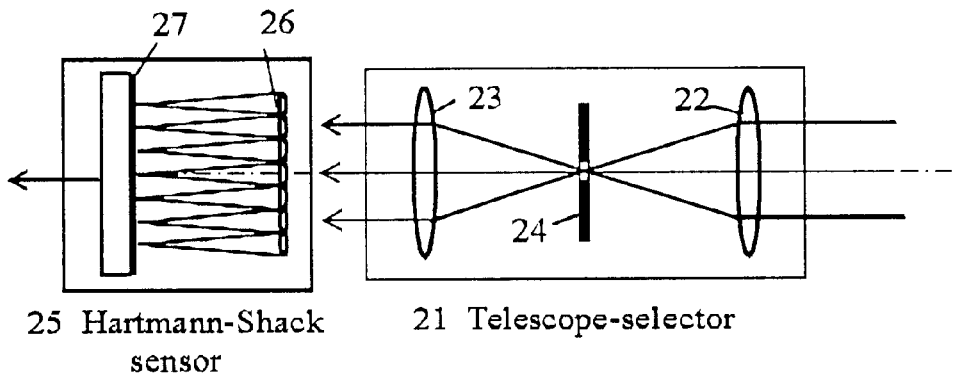
FIG. 20. Course of rays through the telescope-selector of the first embodiment of the device with a normal orientation of the beam from the exit of the acousto-optic deflector.
Figure 21:
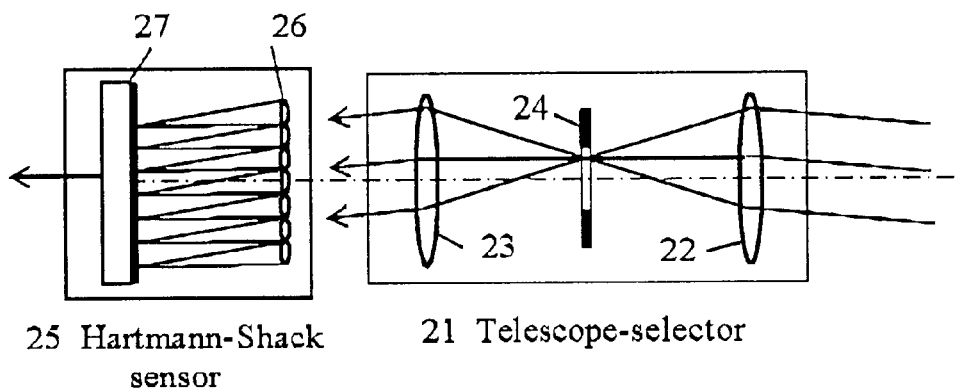
FIG. 21. Course of rays through the telescope-selector of the first embodiment of the device with inclined (upward) impingement of the beam from the exit of the acousto-optic deflector.
Figure 22:
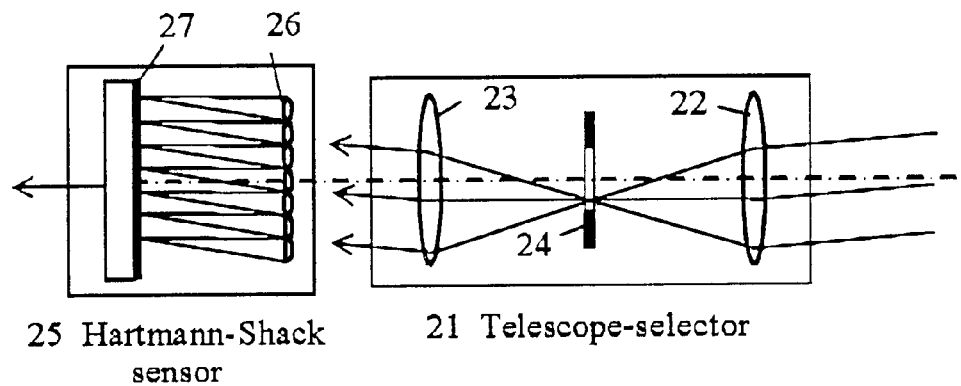
FIG. 22. Course of beams through the telescope-selector of the first embodiment of the device with inclined (downward) impingement of the beam from the exit of the acousto-optic deflector.

During the first measurement, the frequency synthesizer 31 generates the frequencies corresponding to the direction of propagation of the radiation exiting from the acousto-optic deflector parallel to the optical axis of the device, the radiation entering the deflector also being parallel to the optical axis. The course of rays through the telescope-selector 21 and inside the Hartmann-Shack sensor 25 is shown in FIG. 20. In the next measurement, the synthesizer 31 provides frequencies corresponding to the direction of the radiation tilted by one step of the "densified" measuring grid (i.e., ½ or ⅓ or ¼, etc., of the "rarefied" grid of the lenslet array). FIG. 21 shows how the course of beams varies through the telescope-selector 21 and the Hartmann-Shack sensor 25 due to wave front tilting provided by the acousto-optic deflector 18. Deflection in the opposite direction changes the course of rays (FIG. 22).

In the still next measurement, the wave front tilt is again varied by one step. After finishing all steps of the measurements, the data which are stored in the memory of the computer about the positions of the focal images are used for reconstruction of the wave front with higher spatial resolution in accordance with a known algorithm, for example as described in the publication of J. Liang, et al. Objective measurement of the wave aberrations of the human eye using a Hartmann-Shack wavefront sensor. *Journal of the Optical Society of America*: A, 1994, Vol. 11, pp. 1949–1957.

Figure 23:
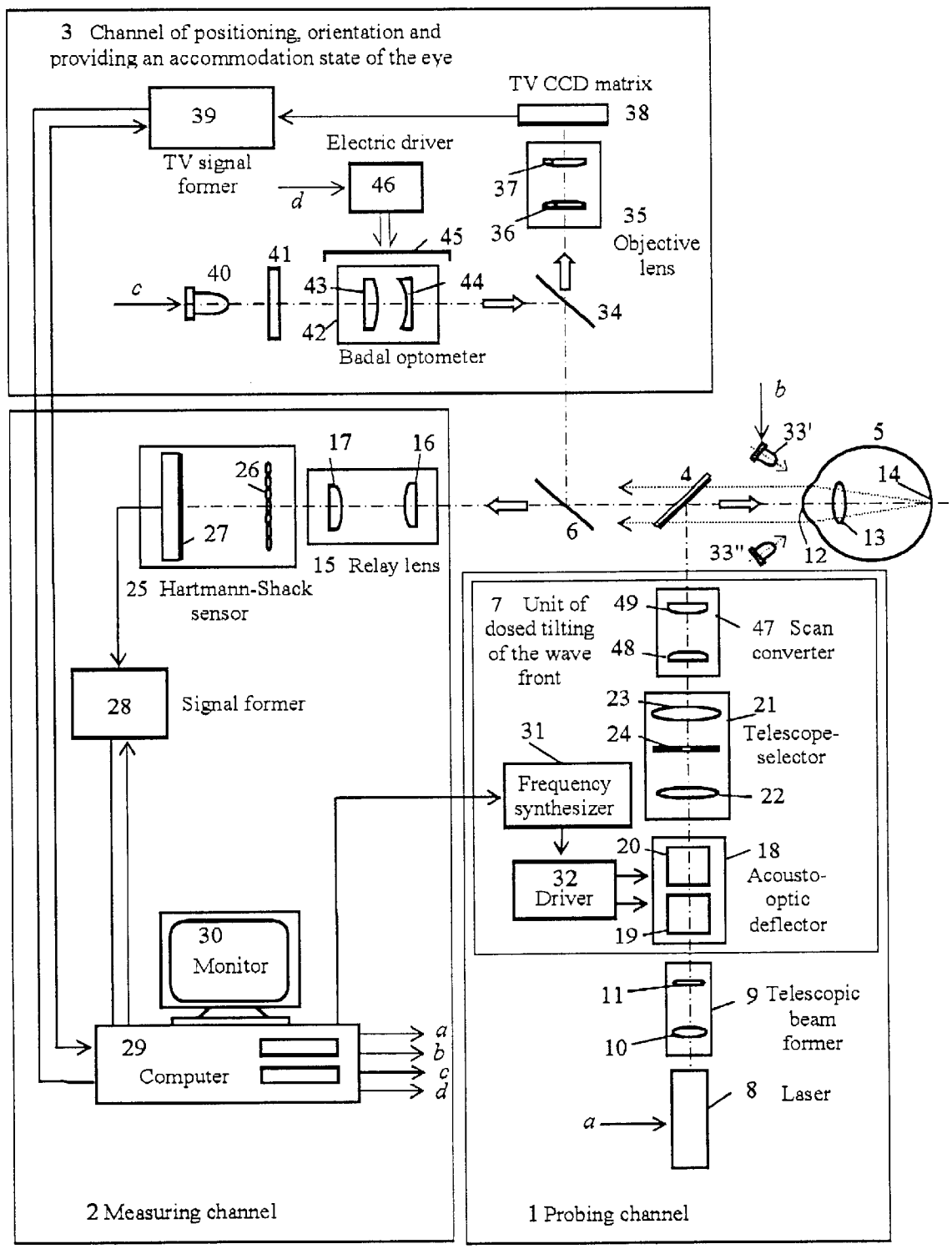
FIG. 23. Functional schematic diagram of the device for measuring wave front aberrations of an eye (second version) and a patient's eye.

Functional schematic diagram of the device for performing the proposed method in accordance with the second embodiment is shown in FIG. 23. In contrast to the first version of the embodiment, the unit 7 of dosed tilting of the wave front is introduced into the probing channel 1 after the telescopic beam former 9, not into the measuring channel 2. Additionally, a scan converter 47 is introduced into the unit 7 itself being composed of two lenses 48 and 49. Scan converter 47 is set at the exit of the telescope-selector 21. The remaining components and their links are the same as in the first embodiment of the device.

Thus, in the second version of the device, the probing channel 1 contains the components 8–11, 18–24, 31, 32 and 47–49, while the unit of dosed tilting of the wave front includes the components 18–24, 31, 32, and 47–49. The measuring channel 2 includes the components 15–17 and 25–30. The channel 3 of positioning, orientation and providing an accommodation state of the eye has the same components as in the first embodiment of the device, namely, it includes the components 33–46.

The device in accordance with the second version of the embodiment functions in the following manner. First of all, a primary orientation and positioning of the patient's eye, as well as its accommodation are performed like in the first embodiment of the device.

The measurement itself starts from the first step, when the laser radiation is introduced into the eye in parallel to the line of sight. Light beam from the laser 8 passes in this case successively through the telescopic beam former 9, the acousto-optic deflector 18, the telescope selector 21, the scan converter 47 and is directed into the eye by the polarization beam splitter 4. Function of the telescopic beam former 9 is formation of axially symmetric beam. Acousto-optic deflector 18 is controlled by a driver 32, and the frequencies of its output control voltages are provided by the frequency synthesizer 31, which is controlled in accordance with the program from the computer 29.

In the first step of measurements, the axis of the laser beam, exiting from the deflector, coincides in the first order of diffraction with the optical axis of the device. The function of the spatial filter-selector 24 is to allow the passing of the radiation only in the first order of diffraction for both directions of deflection. In contrast to the telescope-selector 21 in the first embodiment of the device, magnification of the telescope 21 is chosen so that a narrow beam of light is provided at its exit. Practically, it means that the lens 23 in the second embodiment has a shorter focal length than the same lens in the first version of the device.

Scan converter functions in such a way, that the beam exiting from the center of deflection of the laser beam at the exit of the telescope-selector 21 reaches the cornea in the point of crossing the cornea by the axis of the device. For this purpose, said condition must be satisfied for all orientations at which the laser beam is directed into the eye. The front focus of the lens 48 is arranged to coincide with the center of scanning, and the back focus of the lens 49 must coincide with the apex of the cornea 12.

Figure 24:
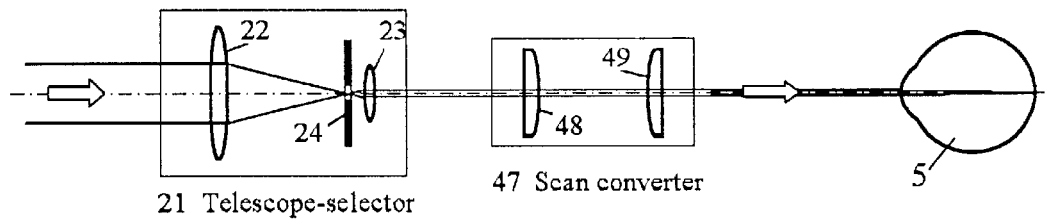
FIG. 24. Course of rays through the telescope-selector and the scan converter (second version of the device) with a normal orientation of the laser beam from the exit of the acousto-optic deflector.
Figure 25:
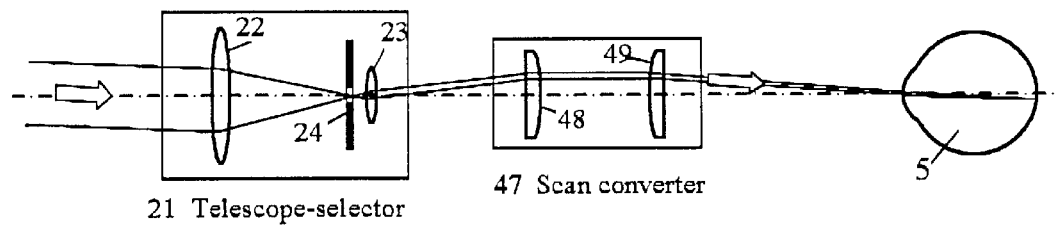
FIG. 25. Course of rays through the telescope-selector and the scan converter (second embodiment of the device) with tilted (downward) laser beam from the exit of the acousto-optic deflector.
Figure 26:
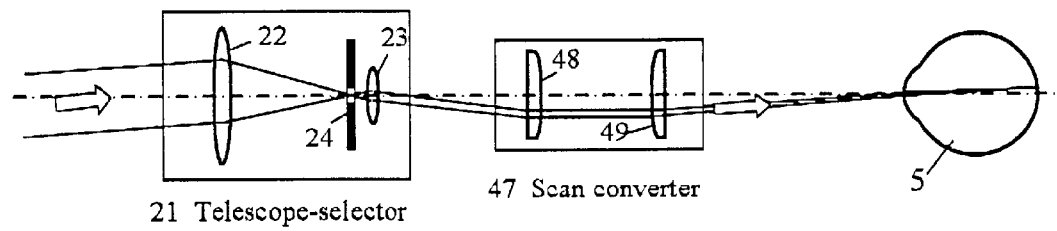
FIG. 26. Course of rays through the telescope-reflector and the scan converter (second embodiment of the device) with tilted (upward) laser beam from the exit of acousto-optic deflector.

Functioning of the scan converter is illustrated by FIGS. 24 through 26. FIG. 24 shows the course of rays through the telescope-selector 21 and the scan converter 47 without additional tilt, and FIGS. 25 and 26 show the course of rays when the laser beam from the exit of the acousto-optic deflector 18 is tilted.

As mentioned above, in the first step of measurements, the laser beam enters the eye, its axis coinciding with the axis of the device. A portion of radiation scattered by the retina exits from the eye, and having passed the components 4, 6, and 15, impinges on the wave front sensor 25. The lenslet array 26 is made so as to provide unambiguous identification of the focal images in the plane of the matrix of photodetectors 27 for a given wide range of wave front distortions.

Signals from the matrix of photodetectors 27 are input to the unit 28 forming the input data for the computer 29, in which all mathematical operations required for the reconstruction of the wave front are performed. In the first step of measurements, the data are stored in the memory of the computer, corresponding to the first position of the focal images created by a "rarefied" lenslet array 26 when normal impingement occurs of the probing laser beam onto the eye 5.

In the second step of measurements, laser beam is directed into the eye through the same point of incidence (which coincides with the intersection of the cornea by the optical axis of the device), but being tilted in regard to the optical axis. This tilt is a result of deflection of the laser beam by the acousto-optic deflector 18 due to supply by the driver 32 of controlling voltages to it, having other frequencies generated by the frequency synthesizer 31 in the second step of measurements.

Data on the positions of the focal images in the plane of the matrix of photodetectors 27, like in the first step, are transferred to the computer 29 through the unit 28 and stored into computer's memory.

Figure 27:
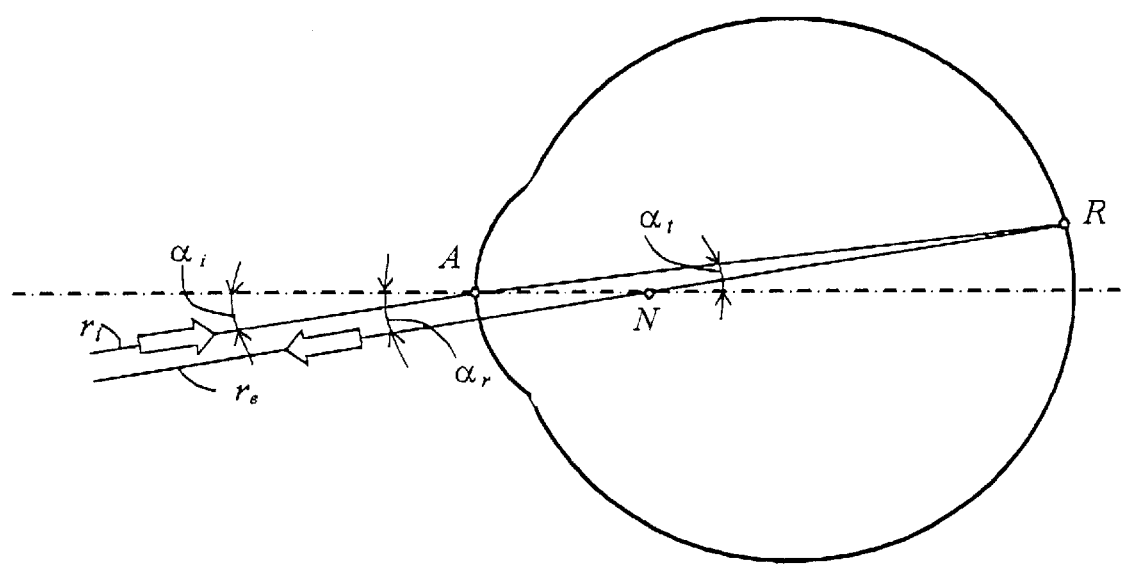
FIG. 27. Tilt of the ray exiting from the eye depending on the tilt of the laser probing beam, directed into the eye (example of Listing's model): $r_f$—probing ray; $r_e$—central ray of radiation exiting from the eye; $?\alpha_i$—angle of impingement of the probing ray; $?\alpha_r$—angle of refraction of the ray which entered the eye; $\alpha_r$—angle of exit from the eye of the central ray; A—point of entry of the probing ray into the eye (apex of the cornea); R—point of crossing of the retina by the probing ray, N—nodal point.

Wave front tilt of the radiation exiting from the eye, is demonstrated by FIG. 27, where the eye is represented by the Listing's schematic eye (reduced model of the eye).

If the incident ray $r_i$, impinges on the eye at an angle $\alpha?_i$ in the point A, which is located on the optical axis, then it will continue its propagation in the eye media at an angle $\alpha?_r$, and will cross the retina in the point R. On its way back, the principal ray $r_e$ of the radiation scattered by the retina must pass through the nodal point N, which is the center of curvature of the cornea. It will be tilted by an angle $\alpha?_r$ to the optical axis. In a some cases, the angle $\alpha?_r$ may not be equal to the angle of incident $\alpha?_i$.

The next step of measurements with farther variation of the angle of incidence of the laser beam onto the eye is similar to the second step. Step-by-step procedures are repeated until the measurements are performed for all wave front tilts, required for filling the densified grid of data. In particular, with a 2 times linearly rarefied lenslet, it is necessary to perform four steps of measurements, with the 3 times rarefication—nine measurements, etc. Farther calculations of the wave front are based on the data for a set of all wave front tilts, which were generated by the acousto-optic deflector 18, i.e., the same as if these calculations were performed due to the measurements with the densified measuring grid or, in other words, with a higher spatial resolution.

It will be understood that each of the elements described above, or two or more together, may also find a useful application in other types of constructions differing from the types described above.

While the invention has been illustrated and described as embodied in method of measurement of wave aberrations of an eye and device for performing the same (versions), it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of measurement of wave aberrations of an eye, the method comprising the steps of probing an eye with a narrow beam of laser radiation; selecting a component of the radiation scattered by a retina and exited back from the eye; partitioning said component into subapertures by a lenslet array, measuring a wave front tilt in each subaperture by determining a shift of a position of a focal spot in regards to an optical axis of each lens of the lenslet array; reconstructing the wave front using the measured tilts in separate subapertures; calculating aberrations of the wave front as measures of wave front deviation from an ideal shape; measuring the wave front tilts in the subapertures several times with a tilt of the whole beam of laser radiation varied in each subsequent measurement by a value within an angular range between neighboring subapertures; and performing the reconstruction of the wave front from data obtained at all tilts of the whole beam of laser radiation.

2. A method as defined in claim 1, wherein said tilt of the whole beam of laser radiation is performed at each probing by tilting a probing laser beam, which enters the same point of the eye aperture.

3. A method as defined in claim 1, wherein said tilt of the whole beam of laser radiation is performed at each probing by deflecting the radiation exiting from the eye.

4. A method as defined in claim 1, or claim 2, or claim 3; comprising said subapertures being designed containing transparent and non-transparent sections, each transparent section being filled with a lenslet, the size of said non-transparent sections being equal or multiple of said transparent sections.

5. A device for measurement of wave aberrations of an eye, the device comprising a probing channel including means for probing an eye with a narrow beam of laser radiation; a measuring channel operative for selecting a component of the radiation scattered by a retina and exited back from the eye, partitioning said component into subapertures by a lenslet array, and measuring a wave front tilt in each subaperture by determining a shift of a position of a focal spot in regards to an optical axis of each lens of the lenslet array; computer means for reconstructing the wave front using measured tilts of the wave front in separate subapertures and calculating aberrations of the wave front as measures of wave front deviation from an ideal shape, said measuring channel being formed so as to measure the wave front tilts in the subapertures several times with a tilt of the whole beam of the laser radiation varied in each subsequent measurement by a value within an angular range between neighboring subapertures, said computing means being formed so as to reconstruct the wave front from data obtained at all tilts of the whole beam of laser radiation.

6. A device as defined in claim 5; and further comprising a polarization beam splitter which separates said probing channel and said measuring channel from one another.

7. A device as defined in claim 5; and further comprising a channel of positioning, orientation and providing an accommodation state of the eye, connected to the measuring channel via a beam splitter.

8. A device as defined in claim 5, wherein said probing means of said probing channel include a laser and a telescopic beam former of radiation.

9. A device as defined in claim 8, wherein said probing channel after a telescopic beam former is provided with a unit of dosed tilting of the wave front.

10. A device as defined in claim 9, wherein said unit of dosed tilting of the wave front consists of two rotating wedges.

11. A device as defined in claim 9, wherein said unit of dosed tilting of the wave front contains an oscillating mirror.

12. A device as defined in claim 9, wherein said unit of dosed tilting of the wave front includes a two-coordinate acousto-optic deflector, a telescope-selector, a scan converter, a driver of the acousto-optic deflector and a frequency synthesizer, so that said two-coordinate acousto-optic deflector, said telescope-selector and said scan converter are arranged in series, said driver having outputs connected to said acousto-optic deflector, said frequency synthesizer having an output connected to an input of said driver and a controlled input linked to said computing means.

13. A device as defined in claim 5, wherein said measuring channel includes a relay lens, said lenslet array, and a matrix of position-sensing photodetectors installed in their foci and connected to a signal former which is linked to said computing means.

14. A device as defined in claim 13, wherein said measuring channel, along a path of radiation exiting from the eye, is provided with a unit of dosed tilting of the wave front.

15. A device as defined in claim 14, wherein said unit of dosed tilting of the wave front is located between said relay lens and said lenslet array.

16. A device as defined in claim 15, wherein said unit of dosed tilting of the wave front consists of a transparent rotating plate, tilted in regards to the axis of rotation, which coincides with optical axis of the measuring channel.

17. A device as defined in claim 15, wherein said unit of dosed tilting of the wave front consists of two rotating wedges.

18. A device as defined in claim 15, wherein said unit of dosed tilting of the wave front contains an oscillating mirror.

19. A device as defined in claim 15, wherein said unit of dosed tilting of the wave front includes a two-coordinate acousto-optic deflector, a telescope-selector, a driver of said acousto-optic deflector and a frequency synthesizer so that said two-coordinate acousto-optic deflector and said telescope-selector are arranged in series, said driver having outputs connected to said acousto-optic deflector, said frequency synthesizer having an output connected to an input of said driver and a controlled input linked to said computing means.

* * * * *